Figure 1:
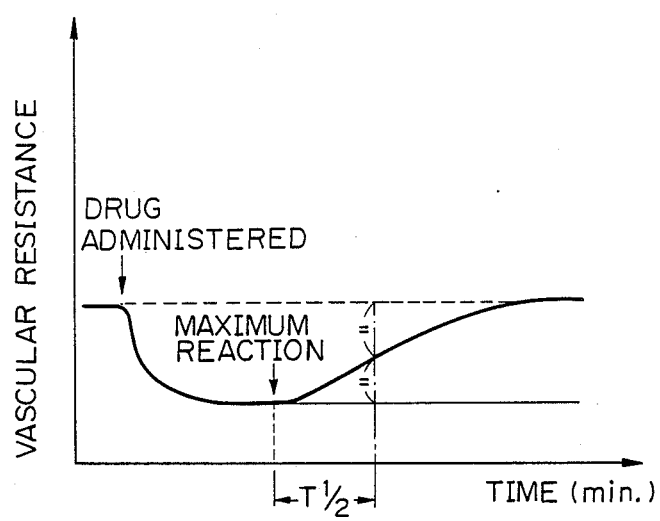

United States Patent [19]

Cho et al.

[11] Patent Number: 4,920,124
[45] Date of Patent: Apr. 24, 1990

[54] N-SUBSTITUTED 3,4-DIHYDROPYRIMIDINE COMPOUNDS AS AGENTS FOR TREATING DISORDERS OF CARDIOVASCULAR SYSTEM

[75] Inventors: Hidetsura Cho, Osaka; Masaru Ueda, Saitama, both of Japan

[73] Assignee: Suntory Limited, Osaka, Japan

[21] Appl. No.: 157,777

[22] Filed: Feb. 19, 1988

[30] Foreign Application Priority Data

Feb. 21, 1987 [JP] Japan ................................ 62-38345

[51] Int. Cl.$^5$ .................. A61K 31/505; C07D 239/02
[52] U.S. Cl. .................................. 514/256; 544/335; 544/229
[58] Field of Search ................. 544/335, 229; 514/256

[56] References Cited

U.S. PATENT DOCUMENTS 4,640,922  2/1987  Cho et al. ............................ 544/335
4,683,234  7/1987  Cho et al. ............................ 544/335

FOREIGN PATENT DOCUMENTS 0103796   3/1983  European Pat. Off. ............ 544/335
162208   11/1985  European Pat. Off. ............ 544/335
195374    9/1986  European Pat. Off. ............ 544/335
62-5968   1/1987  Japan .................................. 544/335

OTHER PUBLICATIONS

Iwanami et al., Chem. Pharm. Bull., vol. 27, No. 6, pp. 1426–1440, (1979).
C. Kashima et al., "Independent Synthesis of Three Types of N–Substituted Dihydrophyrimidines and Their Reactions with Malachite Green", Tetrahedron Letters, vol. 24, No. 2, 1983, pp. 209–212.
D. Nasipuri et al., "Phase-Transfer Catalysis; I.S.-Methylation of 1-Aryl-4,4,6-Trimethyl-2-Thioxo-1,2,3-,4–Tetrahydropyrimidines", Communications, Dec. 1982, pp. 1073–1075.
E. F. Silversmith, J. Org. Chem. 27:4090–4091 (1962).

Primary Examiner—John M. Ford
Assistant Examiner—Robert C. Whittenbaugh
Attorney, Agent, or Firm—Cushman, Darby & Cushman

[57] ABSTRACT

N-substituted 3,4-dihydropyrimidine compounds of the formula:

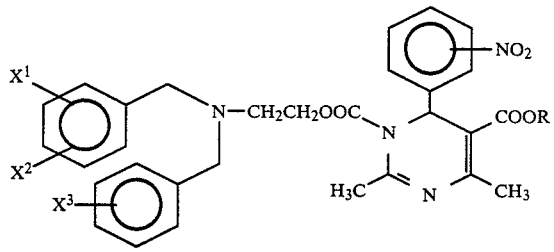

wherein R is straight, branched, cyclic or cyclo-straight alkyl having from one to four carbon atoms; and $X^1$, $X^2$ and $X^3$ are the same or different and are hydrogen, halogen, lower alkyl having from one to four carbon atoms, lower alkoxy having from one to four carbon atoms, nitro, trifluoromethyl, hydroxy, or t-butyldimethylsilyloxy with the proviso that the case wherein $X^1$, $X^2$ and $X^3$ are all hydrogen is not applicable have substantially strong and lasting vasodilative effects. Therefore, the compounds are useful as agents for treating disorders of the cardiovascular system, for example, antihypertensive agents, circulation improver and antianginal agents.

5 Claims, 1 Drawing Sheet

N-SUBSTITUTED 3,4-DIHYDROPYRIMIDINE COMPOUNDS AS AGENTS FOR TREATING DISORDERS OF CARDIOVASCULAR SYSTEM

This invention relates to N-substituted 3,4-dihydropyrimidine compounds of the formula (1):

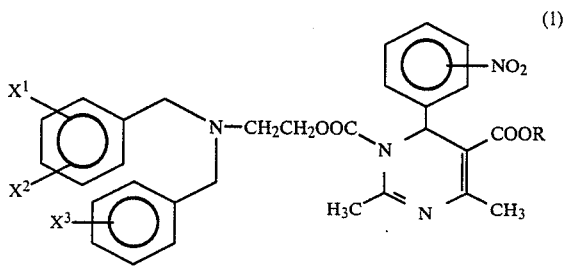

wherein R is straight, branched, cyclic or cyclostraight alkyl having from one to four carbon atoms; and $X^1$, $X^2$ and $X^3$ are the same or different and are hydrogen, halogen, lower alkyl having from one to four carbon atoms, lower alkoxy having from one to four carbon atoms, nitro, trifluoromethyl, hydroxy or t-butyldimethylsilyloxy with the proviso that the case wherein $X^1$, $X^2$ and $X^3$ are all hydrogen is not applicable and an agent for treating disorders of the cardiovascular system.

Since the above dihydropyrimidine compounds of the formula (1) have a strong and long lasting vasodilative effect, said compounds are useful as agents for treating disorders of the cardiovascular system, for example, antihypertensive agents, cerebral circulation improvers and antianginal agents.

Currently antagonists (Ca++ antagonists), which are spotlighted as new agents for treating disorders of the cardiovascular system, have a variety of pharmacological effects and are active not only against hypertension, angina pectoris, cerebral circulation disorder and arrhythmia but also in preventing arteriosclerosis and protentiating the effects of carcinostatic agents. Thus therapeutic uses of Ca++ antagonists continue to increase.

Ca++ antagonists which have been known include Nifedipine, Nicardipine, Verapamil, Diltiazem and the like.

Up to this day, however, dihydropyrimidine derivatives have not often been investigated. Only a few references disclose said derivatives. [For example refer to Silversmith, E. F. J., Org. Chem., 27, 4090 (1962), Nasipuri, D. et al., Synthesis 1073 (1982), Kashima, C., Tetrahedron Letters 209 (1983) and Japanese Patent Public Disclosure No. 73572/59 (Bayer, A. G.)].

This can be considered to be due to the instability and tautomerism of the dihydropyrimidine compounds. But there is room for improvement in the properties of the above-mentioned Ca++ antagonists such as duration of action, organselectivity, stability against light, heat etc. and with respect to side effects.

The inventors thoroughly investigated the Ca++ antagonists which are currently considered to be important. As a result was found that N-substituted 3,4-dihydropyrimidine derivatives have excellent vasodilative effects and high stability. (Refer to Japanese Patent Public Disclosure Nos. 214778/85, 246376/85, 252471/85, 43171/86 and 5968/87.) However, the inventors more eagerly investigated the Ca++ antagonists which have the most excellent vasodilative effects, stability over a long term and reduced toxicity levels. As a result we have found that the N-substituted-3,4-dihydropyrimidine compounds of the formula (1) not only have excellent stability and strong vasodilative effects but also long-term duration.

The present invention provides N-substituted 3,4-dihydroppyrimidine compounds of the formula (1):

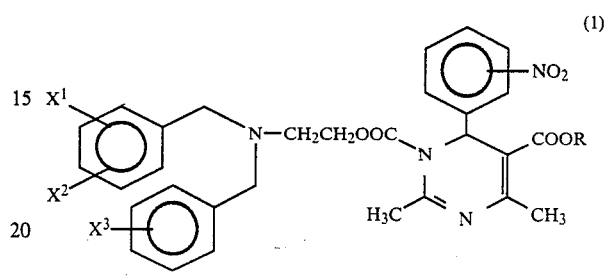

wherein $X^1$, $X^2$, $X^3$ and R are as defined above.

N-substituted 3,4-dihydropyrimidine compounds of the formula (1) can be prepared in the following procedures:

(i) Preparation of the intermediates of the formula (2) and (2'):

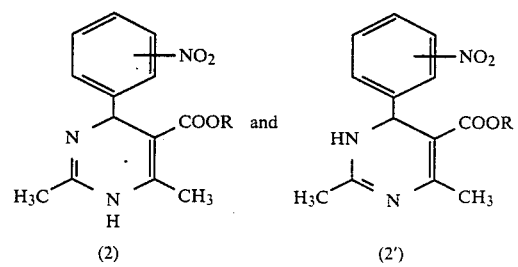

wherein R is as defined above.

A compound of the formula ROH wherein R is as defined above is heated with one equivalent amount of diketene at 100° C.–200° C., preferably 120° C. for 30–60 minutes to give β-ketoester of the formula (3):

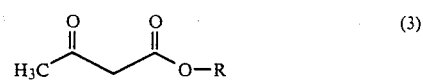

wherein R is as defined above.

Alternatively, a compound of the formula (3) can be obtained by treating a compound of the formula ROH in the presence of an equivalent amount of a base such as trialkylamine at room temperature or treating said compound with said diketene at 0° C., or reacting said compound with diketene in the presence of sodium hydride or potassium hydride.

Benzaldehyde wherein the benzene ring is substituted with nitro group is added to the β-ketoester (3) and the mixture is subjected to dehydration-condensation to produce a benzylidene compound of the formula (4):

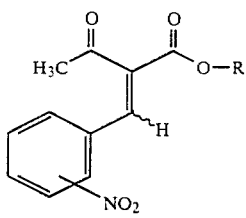 (4)

wherein R is as defined above.

The condensation of the benzylidene (4) with acetamidine or acetamidine hydrochloride produced tetrahydropyrimidine compound (5) of the formula:

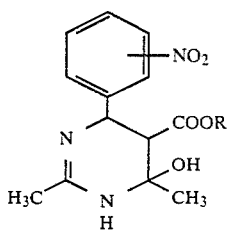 (5)

In order to obtain the compound (5), the above condensation above is carried out in the presence of a base. Preferable bases for use in this procedure include metal alkoxides and metal hydride and suitable solvents include alcohols, ethers and dimethylformamide.

The tetrahydropyrimidine (5) is heated in the presence of a catalyst such as p-toluenesulfonic acid, boron trifluoride or camphor-sulfonic acid, or heated with silica gel, alumina or molecular sieves to produce compounds represented by the formulae (2) and (2') (tautomeric isomers).

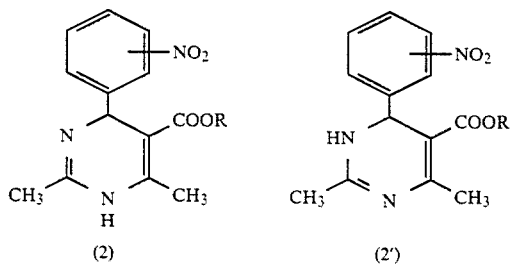

wherein R is as defined above.

The compounds obtained above may be purified by a conventional purification method such as adsorption chromatography, ion-exchange chromatography, partition chromatography, distillation or recrystallization.

(ii) Preparation of N-substituted 3,4-dihydropyrimidine compounds:

The compound represented by the formulae (2) and (2') obtained in the above (i) is dissolved in an organic solvent such as hydrocarbon chlorides, aromatic hydrocarbons or ethers and the solution is added to a solution of phosgene or phosgene dimer in an organic solvent at a temperature not higher than 0° C., preferably $-10°\sim-35°$ C. in the presence of a base, for example, trialkylamine, preferably triethylamine, sodium hydride or potassium hydride. After the reaction is completed, a solution of a N-substituted ethanolamine compound of the formula:

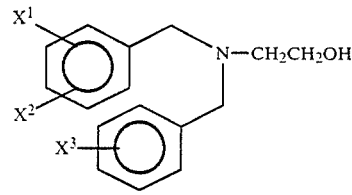

wherein $X^1$, $X^2$ and $X^3$ are as defined above is further added to the reaction at a temperature below room temperature to afford a compound of the formula (1). The organic solvents used in this procedure include any solvents which do not affect the reaction, preferably ethers and hydrocarbon chlorides.

Tautomeric isomers (2) and (2') have vasodilative effects too but the compounds of the formula (1) were synthesized in order to obtain compounds having higher stability and pharmacological activity.

The substituent R at the position 5 of the N-substituted 3,4-dihydropyrimidine compound (1) can be exemplified by an alkyl group such as methyl, ethyl, propyl, isopropyl, n-butyl, sec-butyl or cyclopropylmethyl.

The ester substituent at the position 3 is represented by the formula:

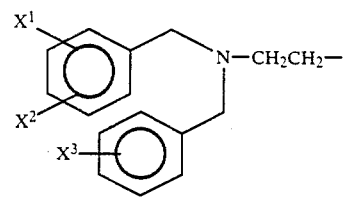

wherein $X^1$, $X^2$ and $X^3$ are exemplified by hydrogen, chloro, fluoro, alkyl such as methyl, ethyl, propyl or butyl, alkoxy such as methoxy, ethoxy, propoxy or butoxy, nitro, trifluoromethyl, hydroxy or t-butyldimethylsilyloxy, with the proviso that the case wherein $X^1$, $X^2$ and $X^3$ are all hydrogen is not applicable.

After the above reaction the products of the formula (1) of this invention can be purified by using conventional methods such as adsorption column chromatography, ion-exchange chromatography or recrystallization.

The compounds of the formula (1) obtained above indicated a strong coronery vasodilative effect in isolated guinea pig hearts and showed strong vasodilative and hypotensive effects in anesthetized dogs and a strong hypotensive effect in conscious spontaneously hypertensive rats (SHR). All of these effects are superior to known drugs such as Nicardipine in terms of potency and duration.

Thus, the compounds (1) of the present invention exhibit superior coronary vasodilative effects in guinea pigs and prove very effective in dogs for increasing the blood flow of vertebral artery, reducing the vascular resistance of vertebral artery and lowering the systemic blood pressure. Because of these effects, the compounds of the present invention will be useful in treating angina pectoris (myocardial infarction), disturbances of cerebral circulation, and hypertension.

For oral administration, the optimum dose range of the compound (1) of this invention is 5–500 mg per day for an adult. Of course, this dose range can be suitably changed depending upon the states of the subjects including age, response, body weight, severity of disease etc.

The invention can be illustrated by the following examples but it should be understood that it is not limited to them. The temperatures stated are in °C. unless otherwise specified.

EXAMPLE 1

3-[2-{N-benzyl-N-(3,4-dichlorobenzyl)amino}ethoxycarbonyl]-5-isopropoxycarbonyl-2,6-dimethyl-4-(2-nitrophenyl)-3,4-dihydropyrimidine

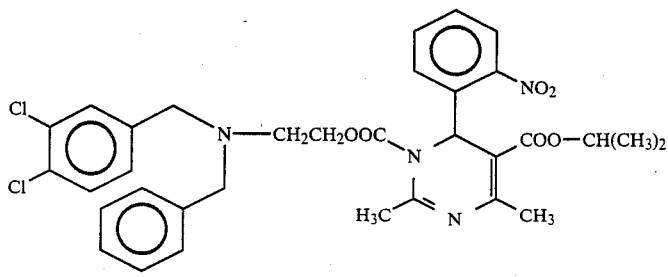

317 mg of 5-isopropoxycarbonyl-2,6-dimethyl-4-(2-nitrophenyl)-1,4(3,4)-dihydropyrimidine and 0.83 ml of triethylamine were dissolved in 30 ml of tetrahydrofuran (THF) and the solution was chilled at −23° C. 60 μl of phosgene dimer was added to this solution, followed by stirring for one hour.

To the mixture, a solution of 311 mg of 2-{N-benzyl-N-(3,4-dichlorobenzyl)amino}ethanol in 10 ml of THF was added at 0° C., followed by stirring for 20 hours at room temperature. The reaction mixture was diluted with water and extracted with chloroform. After drying the extract, the solvent was evaporated and the residue (0.7 g) was subjected to chromatography on silica gel (solvent: benzeneacetone) to produce 0.33 g of the object compound (yield 50%). The physicochemical data of the compound are shown in Table 1.

EXAMPLES 2-17

The procedures of Example 1 were repeated in Examples 2-17 and the resulting comounds had the physicochemical data shown in Table 1.

PREPARATION 1

2-{N-benzyl-N-(3,4-dichlorobenzyl)amino}ethanol (a) Triethylamine method 38.8 g of 3,4-dichlorobenzyl chloride was added to a solution of 25 g of N-benzylethanolamine and 28 ml of triethylamine in 300 ml of THF, followed by reflux for 24 hours. After evaporating the solvent, 10% HCl was added to the residue to produce hydrochloride salt of the object compound. The thus obtained crystals were neutralized by adding 10% sodium hydroxide solution and extracted with isopropylether. After drying the extract, the solvent was evaporated to produce the object compound (29 g, yield 57%).

(b) Potassium carbonate method

To a solution of 13 g of 3,4-dichlorobenzyl chloride and 9.15 g of N-benzylethanolamine in 150 ml of dimethylformamide (DMF), 9 g of anhydrous potassium carbonate was added and the mixture was vigorously stirred. After stirring for 24 hours, the reaction mixture was acidified by adding 10% HCl and extracted with isopropyl ether. The aqueous phase was made basic with 10% sodium hydroxide solution and extracted with isopropyl ether. The extract was dried and the solvent was evaporated to produce the object compound (10.8 g, yield 57%).

EXAMPLE 18

3-[2-{N-benzyl-N-(3-t-butyldimethylsilyloxy)benzyl}aminoethoxycarbonyl]-5-isopropoxycarbonyl-2,6-dimethyl-4-(2-nitrophenyl)-3,4-dihydropyrimidine

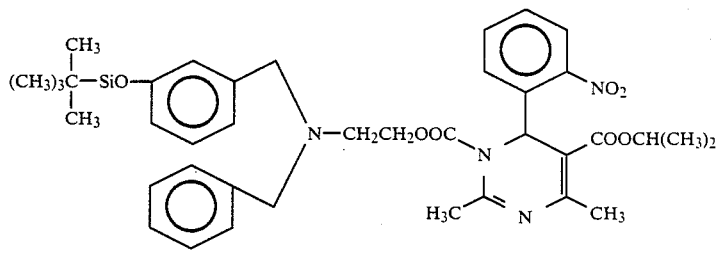

To a solution of 182 μl of phosgene dimer in 6 ml of THF, a solution of 2.4 ml of triethylamine and 806 mg of 5-isopropoxycarbonyl-2,6-dimethyl-4-(2-nitrophenyl)-1,4(3,4)-dihydropyrimidine in 12 ml of THF was added under stirring at −23° C., followed by stirring for one hour. To this mixture, a solution of 1.13 g of 2-{N-benzyl-N-(3-t-butyldimethylsilyloxy)benzyl-]aminoethanol in 6 ml of THF was thereafter added at 0° C., followed by stirring for one hour. After stirring at room temperature for additional 2 hours, the reaction mixture was diluted with water and extracted with chloroform. After drying the extract, the solvent was evaporated. The residue (1.8 g) was subjected to chromatography on silica gel (solvent: ethyl acetate-n-hexane) to produce 923 mg of the object compound (51%).

PREPARATION 2

2-{N-benzyl-N-(3-t-butyldimethylsilyloxy)benzyl-}aminoethanol

To a solution of 9.17 g of methyl 3-hydroxybenzoate in 40 ml of DMF, 10 g of t-butyldimethylsilyl chloride and 9.0 g of imidazol were added, followed by stirring for 16 hours at room temperature. The reaction mixture was diluted with water and extracted with ether. After drying the extract, the solvent was evaporated and the residue was subjected to chromatography on silica gel. The ester compound (9.5 g) obtained above was dissolved in 95 ml of ether and lithium alminum hydride was added to the solution at 0° C., followed by stirring for 90 minutes at room temperature. Excess reagents were decomposed by adding ether and water. The supernatants was dried and concentrated to produce 10.2 g of the alcohol compound. To a solution of the compound (5.0 g) in 60 ml of THF, 4.4 ml of triethylamine and 2.28 ml of methanesulfonyl chloride were added under stirring at −23° C. and the mixture was stirred for one hour. Thereafter, a solution of 3.65 g of lithium bromide in 45 ml of acetone was added to the mixture at −23° C., followed by stirring for one hour. After stirring for additional 6 hours at room temperature, the solvent was evaporated and the residue was diluted with water and extracted with ether. After drying the extract, the solvent was evaporated leaving a residue (a bromide compound) (5.42 g). To a solution of 1.3 g of the compound in 5 ml of THF, a solution of 0.6 ml of triethylamine and 0.54 g of N-benzylethanolamine in 5 ml of THF was added. After refluxing for 18 hours, the reaction mixture was diluted with water and extract, the solvent was evaporated to produce the object compound (1.26 g).

EXAMPLE 19

3-[2-{N-benzyl-N-(3-hydroxybenzyl)amino}ethoxycarbonyl]-5-isopropoxycarbonyl-2,6-dimethyl-4-(2-nitrophenyl)-3,4-dihydropyrimidine

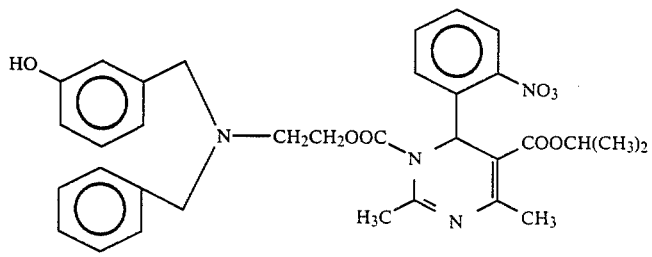

155 mg of potassium fluoride was added to a solution of 191 mg of the compound obtained in Example 18 in 3 ml of acetonitrile. After stirring for 24 hours at room temperature, the reaction mixture was diluted with water and extracted with ethyl acetate. The extract was dried and the solvent was evaporated. The residue was subjected to chromatography on silica gel (solvent: ethyl acetate-n-hexane) to produce the object compound (99 mg, yield 62%).

EXAMPLE 24

3-[2-{N-benzyl-N-(3,4-dichlorobenzyl)amino}ethoxycarbonyl]-5-isopropoxycarbonyl-2,6-dimethyl-4-(3-nitrophenyl)-3,4-dihydropyrimidine

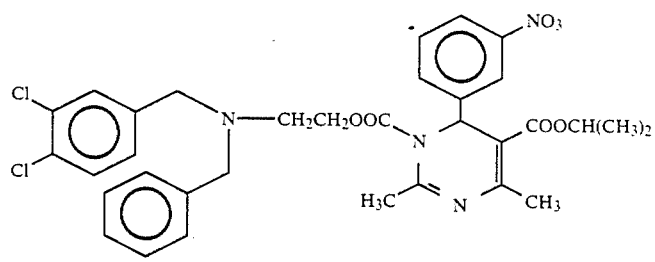

To a solution of 793 mg of 5-isopropoxycarbonyl-2,6-dimethyl-4-(3-nitrophenyl)-1,4(3,4)-dihydro-pyrimidine and 2 ml of triethylamine in 20 ml of anhydrous methylene chloride, 150 µl of phosgene dimer was gradually added at −23° C., followed by stirring for one hour. To the mixture, a solution of 0.78 g of N-{N-benzyl-N-(3,4-dichlorobenzyl)amino}ethanol in 20 ml of anhydrous methylene chloride was added at −23° C., followed by stirring for one hour. The reaction mixture was diluted with water and extracted with ether. After drying the extract, the solvent was evaporated and the residue was subjected to chromatography on silica gel (solvent: ethyl acetate-n-hexane) to produce the object compound (1.10 g, yield 67.5%).

TABLE 1

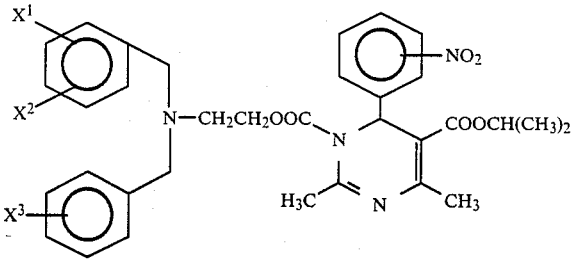

| Ex. No. | Compound (1) (position of nitro group) | Yield (%) | Description (m.p., if any) | IR spectrum (CHCl₃, cm⁻¹) | NMR spectrum (270 MHz, CDCl₃, δ ppm) |
|---|---|---|---|---|---|
| 1 | (2-nitro)<br>X¹=3-chloro<br>X²=4-chloro<br>X³=hydrogen | 50 | crystals<br>m.p.<br>81–85°<br>(isopropyl ether) | 1735<br>1705 | 1.04(3H,d, J=6Hz),<br>1.25(3H,d,J=6Hz), 2.27(3H,s),<br>2.47(3H,s), 2.80(2H,t,J=6Hz),<br>3.57(2H,s), 3.61(2H,s),<br>4.12–4.39(2H,m), 4.93–5.08(1H,m),<br>6.82(1H,s), 7.05–7.80(12H,m) |
| 2 | (2-nitro)<br>X¹=4-methoxy group<br>X²=X³=hydrogen | 49 | crystals<br>m.p.<br>89–90°<br>(chloroform-n-hexane) | 1730<br>1700 | 1.04(3H,d,J=1.04(3H,d,J=6Hz),<br>1.25(3H,d,J=6Hz), 2.24(3H, s),<br>2.48(3H,s), 2.78(2H,t,J=6Hz),<br>3.56(2H,s), 3.59(2H,s),<br>3.78(3H,s), 4.12–4.39(2H,m),<br>4.94–5.09(1H,m), 6.75–7.80(14H,m) |
| 3 | (2-nitro)<br>X¹=4-fluoro<br>X²=X³=hydrogen | 70 | crystals<br>m.p.<br>100–101°<br>chloroform-n-hexane) | 1725<br>1695 | 1.04(3H,d, 6Hz),<br>1.25(3H,d,J=6Hz), 2.24(3H,s),<br>2.48(3H,s), 2.78(2H,t,J=6Hz),<br>3.50–3.70(4H,m), 4.11–4.40(2H,m),<br>4.93–5.11(1H,m), 6.80–7.82(14H,m) |
| 4 | (2-nitro)<br>X¹=4-chloro<br>X²=X³=hydrogen | 51 | crystals<br>m.p.<br>93–94°<br>(isopropyl ether) | 1730<br>1700 | 1.04(3H,d,J=6Hz),<br>1.25(3H,d,J=6Hz), 2.24(3H,s),<br>2.48(3H,s), 2.78(2H,t,J=6Hz),<br>3.50–3.69(4H,m), 4.12–4.38(2H,m),<br>4.93–5.10(1H,m), 6.83(1H,s),<br>7.10–7.80(13H,m) |
| 5 | (2-nitro)<br>X¹=4-methyl<br>X²=X³=hydrogen | 62 | crystals<br>m.p.<br>84–86°<br>(isopropyl ether) | 1735<br>1700 | 1.04(3H,d,J=6Hz),<br>1.25(3H,d,J=6Hz), 2.24(3H,s),<br>2.31(3H,s), 2.48(3H,s),<br>2.78(2H,t,J=6Hz), 3.58(2H,s),<br>3.60(2H,s), 4.11–4.38(2H,m),<br>4.92–5.09(1H,m), 6.83(1H,s),<br>7.00–7.80(13H,m) |
| 6 | (2-nitro)<br>X¹=X³=4-fluoro<br>X²=hydrogen | 61 | oil | 1720<br>1695 | 1.05(3H,d, J=6Hz),<br>1.25(3H,d,J=6Hz), 2.25(3H,s),<br>2.48(3H,s), 2.77(2H,t,J=6Hz),<br>3.53(2H,d,J=17Hz),<br>3.58(2H,d,J=17Hz),<br>4.10–4.38(2H,m), 4.94–5.10(1H,m),<br>6.82(1H,s), 6.84–7.80(12H,m) |
| 7 | (2-nitro)<br>X¹=3-nitro<br>X²=X³=hydrogen | 56 | crystals<br>m.p.<br>67–72°<br>(isopropyl ether) | 1730<br>1700 | 1.04(3H,d,J=6Hz),<br>1.23(3H,d,J=6Hz), 2.27(3H,s),<br>2.47(3H,s), 2.85(2H,t,J=6Hz),<br>3.64(2H,s), 3.73(2H,s),<br>4.14–4.42(2H,m), 4.92–5.08(1H,m),<br>6.80(1H,s), 7.16–8.20(13H,m) |
| 8 | (2-nitro)<br>X¹=4-nitro<br>X²=X³=hydrogen | 56 | crystals<br>m.p.<br>86–90°<br>(isopropyl ether) | 1730<br>1700 | 1.06(3H,d,J=6Hz),<br>1.25(3H,d, J=6Hz), 2.25(3H,s),<br>2.48(3H,s), 2.83(2H,t,J=6Hz),<br>3.55–3.80(4H,m), 4.15–4.42(2H,m),<br>4.95–5.12(1H,m), 6.83(1H,s),<br>7.16–8.20(13H,m) |
| 9 | (2-nitro)<br>X¹=2-fluoro<br>X²=X³=hydrogen | 51 | crystals<br>m.p.<br>110–112°<br>(isopropyl ether) | 1730<br>1700 | 1.03(3H,d,J=6Hz),<br>1.24(3H,d,J=6Hz), 2.24(3H,s),<br>2.48(3H,s), 2.80(2H,t,J=6Hz),<br>3.64(2H,s), 3.70(2H,s),<br>4.15–4.40(2H,m), 4.93–5.08(1H,m),<br>6.83(1H,s), 6.91–7.79(13H,m) |
| 10 | (2-nitro)<br>X¹=3-methoxy<br>X²= X³=hydrogen | 59 | crystals<br>m.p.<br>106–108°<br>(isopropyl ether) | 1730<br>1700 | 1.03(3H,d,J=6Hz),<br>1.24(3H,d,J=6Hz), 2.28(3H,s),<br>2.49(3H,s), 2.81(2H,t,J=6Hz),<br>3.61(2H,s), 3.62(2H,s),<br>3.79(3H,s), 4.13–4.39(2H,m),<br>4.94–5.08(1H,m), 6.71–7.79(14H,m) |
| 11 | (2-nitro)<br>X¹=3-fluoro<br>X²=X³=hydrogen | 48 | crystals<br>m.p.<br>105–107°<br>(isopropyl | 1725<br>1700 | 1.04(3H,d,J=6Hz),<br>1.24(3H,d,J=6Hz), 2.26(3H,s),<br>2.47(3H,s), 2.81(2H,t,J=6Hz),<br>3.62(4H,s), 4.10–4.39(2H,m), |

TABLE 1-continued (1)

[Structure: X¹, X² substituted benzyl and X³ substituted benzyl groups attached to N—CH₂CH₂OOC—N, with the N bearing a CH group connected to a 2-nitrophenyl ring and to a C=C bearing COOCH(CH₃)₂, the latter carbon bonded to C(CH₃)=N—C(CH₃) forming a dihydropyrazine-like ring with H₃C and CH₃ substituents]

| Ex. No. | Compound (1) (position of nitro group) | Yield (%) | Description (m.p., if any) | IR spectrum (CHCl₃, cm⁻¹) | NMR spectrum (270 MHz, CDCl₃, δ ppm) |
|---|---|---|---|---|---|
| 12 | (2-nitro)<br>X¹=2-nitro<br>X²=X³=hydrogen | 67 | crystals<br>m.p.<br>97–99°<br>(isopropyl<br>ether) | 1725<br>1700 | 4.91–5.08(1H,m), 6.75–7.80(14H,m)<br>1.04(3H,d,J=6Hz),<br>1.25(3H,d,J=6Hz), 2.24(3H,s),<br>2.48(3H,s), 2.79(2H,t,J=6Hz),<br>3.61(2H,s), 3.97(2H,s),<br>4.09–4.32(2H,m), 4.91–5.10(1H,m),<br>6.80(1H,s), 7.10–7.90(13H,m) |
| 13 | (2-nitro)<br>X¹=2-chloro<br>X²=X³=hydrogen | 28 | crystals<br>m.p.<br>105–106°<br>(isopropyl<br>ether) | 1725<br>1700 | 1.03(3H,d,J=6Hz),<br>1.25(3H,d,J=6Hz), 2.23(3H,s),<br>2.47(3H,s), 2.83(2H,t,J=6Hz),<br>3.67(2H,s), 3.75(2H,s),<br>4.15–4.40(2H,m), 4.96–5.08(1H,m),<br>6.81(1H,s), 7.10–7.75(13H,m) |
| 14 | (2-nitro)<br>X¹=3-chloro<br>X²=X³=hydrogen | 27 | crystals<br>m.p.<br>77–79°<br>(isopropyl<br>ether-n-<br>hexane) | 1730<br>1700 | 1.04(3H,d,J=6Hz),<br>1.25(3H,d,J=6Hz), 2.27(3H,s),<br>2.47(3H,s), 2.80(2H,t,J=6Hz),<br>3.60(2H,s), 3.61(2H,s),<br>4.15–4.40(2H,m), 4.95–5.10(1H,m),<br>6.83(1H,s), 7.10–7.80(13H,m) |
| 15 | (2-nitro)<br>X¹=2-chloro<br>X²=4-chloro<br>X³=hydrogen | 18 | oil | 1730<br>1700 | 1.05(3H,d,J=6Hz),<br>1.25(3H,d,J=6Hz), 2.24(3H,s),<br>2.48(3H,s), 2.82(2H,t,J=6Hz),<br>3.65(2H,brs), 3.70(2H,s),<br>4.18–4.40(2H,m), 4.95–5.10(1H,m),<br>6.82(1H,s), 7.10–7.80(12H,m) |
| 16 | (2-nitro)<br>X¹=4-trifluoro-<br>methyl<br>X²=X³=hydrogen | 15 | crystals<br>m.p.<br>106–107°<br>(n-hexane) | 1730<br>1700 | 1.05(3H,d,J=6Hz),<br>1.25(3H,d,J=6Hz), 2.23(3H,s),<br>2.47(3H,s), 2.81(2H,t,J=6Hz),<br>3.58–3.71(4H,m), 4.22(1H,d,J=17Hz),<br>4.34(1H,d,J=17Hz), 5.05(1H,m),<br>6.86(1H,s), 7.17–7.78(13H,m) |
| 17 | (2-nitro)<br>X¹=3-methoxy<br>X²=4-methoxy<br>X³=hydrogen | 10 | oil | 1730<br>1700 | 1.03(3H,d,J=6Hz),<br>1.24(3H,d,J=6Hz), 2.26(3H,s),<br>2.46(3H,s), 2.81(2H,t,J=6Hz),<br>3.58(2H,s), 3.60(2H,s),<br>3.86(3H,s), 3.87(3H,s),<br>4.10–4.40(2H,m), 4.96–5.05(1H,m),<br>6.82(1H,s), 6.76–7.79(12H,m) |
| 18 | (2-nitro)<br>X¹=3-t-butyl-<br>dimethyl-<br>silyloxy<br>X²=X³=hydrogen | 51 | oil | 1730<br>1700 | 0.18(6H,s), 0.98(9H,s),<br>1.03(3H,d,J=6Hz),<br>1.24(3H,d,J=6Hz),<br>2.25(3H,s), 2.47(3H,s),<br>2.80(2H,t,J=6Hz), 3.57(2H,s),<br>3.61(2H,s), 4.10–4.40(2H,m),<br>4.95–5.05(1H,m), 6.66–7.78(13H,m) |
| 19 | (2-nitro)<br>X¹=3-hydroxy<br>X²=X³=hydrogen | 62 | oil | 3400<br>1730<br>1700 | 1.14(3H,d,J=6Hz),<br>1.27(3H,d,J=6Hz), 2.24(3H,s),<br>2.53(3H,s), 3.35–3.45(2H,m),<br>3.60–3.80(4H,m), 4.20–4.40(2H,m),<br>5.00–5.18(1H,m), 6.70–7.78(13H,m) |
| 20 | (2-nitro)<br>X¹=4-chloro<br>X²=hydrogen<br>X³=4-nitro | 32 | oil | 1695<br>1725 | 1.07(3H,d,J=6Hz),<br>1.26(3H,d,J=6Hz), 2.25(3H,s),<br>2.49(3H,s), 2.82(2H,t,J=6Hz),<br>3.56(1H,d,J=14Hz),<br>3.65(1H,d,J=14Hz),<br>3.67(1H,d,14Hz),<br>3.75(1H,d,J=14Hz), 4.22(1H,m),<br>4.34(1H,m), 5.06(1H,m),<br>6.85(1H,s), 7.2–8.1(12H,m) |
| 21 | (2-nitro)<br>X¹=3-chloro<br>X²=4-chloro<br>X³=4-methoxy | 32 | oil | 1700<br>1730 | 1.05(3H,d,J=6Hz),<br>1.25(3H,d,J=6Hz), 2.27(3H,s),<br>2.47(3H,s), 2.78(2H,t,J=6Hz),<br>3.55(3H,s), 3.79(4H,s),<br>4.20(1H,m), 4.30(1H,m),<br>5.02(1H,m), 6.82(1H,s), |

TABLE 1-continued

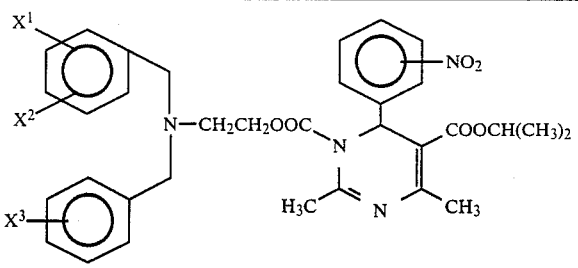
(1)

| Ex. No. | Compound (1) (position of nitro group) | Yield (%) | Description (m.p., if any) | IR spectrum (CHCl$_3$, cm$^{-1}$) | NMR spectrum (270 MHz, CDCl$_3$, δ ppm) |
|---|---|---|---|---|---|
| 22 | (2-nitro) X$^1$=3-chloro X$^2$=hydrogen X$^3$=4-chloro | 62 | crystals m.p. 103–105° (isopropyl ether-n-hexane) | 1695 1725 | 7.1–7.8(11H,m) 1.05(3H,d,J=6Hz), 1.25(3H,d,J=6Hz), 2.27(3H,s), 2.47(3H,s), 2.79(2H,t,J=6Hz), 3.58(2H,s), 3.59(2H,s), 4.21(1H,m), 4.32(1H,m), 5.02(1H,m), 6.82(1H,s), 7.2–7.8(12H,m) |
| 23 | (2-nitro) X$^1$=3-chloro X$^2$=4-chloro X$^3$=4-hydroxy | 44 | powder | 1695 1725 | 1.04(3H,d,J=6Hz), 1.24(3H,d,J=6Hz), 2.28(3H,s), 2.49(3H,s), 2.77(2H,t,J=6Hz), 3.50(2H,s), 3.55(2H,s), 4.19(1H,m), 4.32(1H,m), 5.04(1H,m), 6.27(1H,brs), 6.81(1H,s), 6.7–7.8(11H,m) |
| 24 | (3-nitro) X$^1$=3-chloro X$^2$=4-chloro X$^3$=hydrogen | 68 | oil | 1700 1720 | 1.17(3H,d,J=6Hz), 1.26(3H,d,J=6Hz), 2.34(3H,s), 2.45(3H,s), 2.77–2.88(2H,m), 3.58(2H,s), 3.62(2H,s), 4.28–4.43(2H,m), 5.06(1H,m), 6.24(1H,s), 7.12–8.18(12H,m) |
| 25 | (2-nitro) X$^1$=2-chloro X$^2$=6-chloro X$^3$=hydrogen | 16 | oil | 1700 1730 | 1.04(3H,d,J=6Hz), 1.26(3H,d,J=6Hz), 2.21(3H,s), 2.47(3H,s), 2.84(2H,m), 3.66(2H,brs), 3.93(2H,brs), 4.18–4.32(2H,m), 4.95–5.10(1H,m), 6.79(1H,s), 7.08–7.80(12H,m) |

EXAMPLE 26

The pharmacological effect (ED$_{30}$) of the compounds of the present invention with respect to the vascular resistance of the vertebral artery in anesthetized dogs was tested by the following procedure.

TEST METHOD

Adult dogs of either sex (7~14 kg in body weight) were anesthetized with at first thiopental sodium (35 mg/kg, intraperitoneal), anesthetized with urethane (400 mg/kg, intravenous) and chloralose (60 mg/kg, intravenous) and kept under artificial respiration throughout the experiment. After thoracotomy at the left first intercostal space, the vertebral artery was exposed and blood flow was measured with intracorporeal flow probe connected to an electromagnetic flowmeter (MF-27, Nihon Kohden).

At the same time, continuous measurement of the following parameters was made: systemic blood pressure (mean pressure) at the right femoral artery, the limb lead II ECG, the heart rate with a tachometer triggered by the R wave of ECG, and the vascular resistance determined by loading a electronic divider unit (EO-601 G, Nihon Kohden) with the mean values of blood pressure and vertebral artery blood flow. All of these parameters were recorded simultaneously on a polygraph (RM-600, Nihon Kohden).

All the test compounds were injected through a cannula inserted into the femoral vein.

The ED$_{30}$ (μg/kg) values obtained by intravenous injection are listed in Table 2, wherein the Compound Numbers are keyed to the Example Numbers.

TABLE 2

| Compound Example No. | ED$_{30}$ (μg/Kg) |
|---|---|
| 1 | 2.1 |
| 2 | 1.8 |
| 3 | 2.6 |
| 4 | 2.9 |
| 5 | 2.8 |
| 6 | 1.3 |
| 9 | 2.3 |
| 10 | 1.8 |
| 11 | 2.1 |
| 13 | 4.7 |

EXAMPLE 27

Selected compounds of the present invention were tested for their ability to reduce the resistance of the vertebral artery in anesthetized dogs.

Test method:

The animals were injected with the ED$_{30}$ doses of test compounds and the time course of changes in the vascular resistance were studied in the same manner as in Example 26. The time course of changes can be as shown schematically in FIG. 1. From the curve shown in FIG. 1, the values of $T_{\frac{1}{2}}$ (min) (the time to reach 50% of the resistance drop) were calculated. The results are shown in Table 3, in which the compound numbers correspond to the Example numbers.

TABLE 3

| Compound Example No. | $T_{\frac{1}{2}}$(min) |
| --- | --- |
| 1 | >25.0 |
| 2 | 8.2 |
| 14 | 10.6 |
| 15 | >20.0 |
| 16 | 7.9 |
| 20 | 10.2 |
| 21 | 20.0 |
| 22 | 19.5 |
| 24 | 16.0 |
| 25 | 11.7 |

What is claimed is:

1. A N substituted 3,4-dihydropyrimidine compound of the formula:

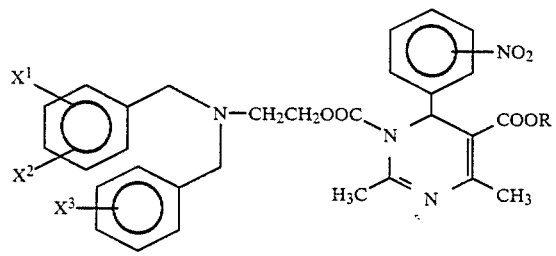

wherein R is a straight or branched cyclic or cyclo straight alkyl having from one to three carbon atoms, and $X^1$, $X^2$ and $X^3$ are the same or different and are hydrogen, halogen, lower alkyl having from one to four carbon atoms, lower alkoxy having from one to four carbon atoms, nitro, trifluoromethyl, hydroxy, or t-butyldimethylsilyloxy with the proviso that the case where $X^1$, $X^2$ and $X^3$ are all hydrogen is not applicable.

2. A compound according to claim 1 wherein halogen is chloro or fluoro.

3. A compound according to claim 1 wherein lower alkyl having from one to four carbon atoms is methyl.

4. A compound according to claim 1 wherein lower alkoxy having from one to four carbon atoms is methoxy.

5. A composition for treating disorders of the cardiovascular system selected from the group consisting of hypertension, cerebral circulation disorders and angina, comprising a N-substituted 3,4-dihydropyrimidine compound of the formula:

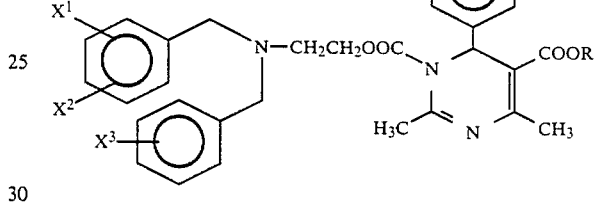

wherein $X^1$, $X^2$, $X^3$ and R as defined in claim 1, in an amount effective for treating said disorders of the cardiovascular system, and a pharmaceutically acceptable carrier.

* * * * *